(12) United States Patent
Kuratsune et al.

(10) Patent No.: US 8,233,960 B2
(45) Date of Patent: Jul. 31, 2012

(54) METHOD AND DEVICE FOR DIAGNOSING CHRONIC FATIGUE SYNDROME (CFS) BY USING NEAR INFRARED SPECTRUM

(75) Inventors: Hirohiko Kuratsune, Osaka (JP); Akikazu Sakudo, Osaka (JP); Kazuyoshi Ikuta, Osaka (JP)

(73) Assignees: Fatigue Science Laboratory Inc., Osaka-shi (JP); Osaka University, Suita-shi (JP); Hirohiko Kuratsune, Toyonaka-shi (JP)

( * ) Notice: Subject to any disclaimer, the term of this patent is extended or adjusted under 35 U.S.C. 154(b) by 1113 days.

(21) Appl. No.: 11/914,755

(22) PCT Filed: May 15, 2006

(86) PCT No.: PCT/JP2006/309656
§ 371 (c)(1),
(2), (4) Date: Nov. 18, 2007

(87) PCT Pub. No.: WO2006/123611
PCT Pub. Date: Nov. 23, 2006

(65) Prior Publication Data
US 2008/0198378 A1    Aug. 21, 2008

(30) Foreign Application Priority Data
May 18, 2005 (JP) .................. 2005-146048

(51) Int. Cl.
*A61B 5/05* (2006.01)
(52) U.S. Cl. ........ 600/407; 600/473; 600/476; 600/309; 600/310; 600/322; 600/323; 600/326; 600/328

(58) Field of Classification Search .......... 600/309, 600/310, 322, 323, 326, 328, 407, 473, 476
See application file for complete search history.

(56) References Cited

U.S. PATENT DOCUMENTS

| 6,438,396 B1 * | 8/2002 | Cook et al. ............ 600/310 |
| 2002/0177778 A1 * | 11/2002 | Averback et al. ........ 600/476 |
| 2004/0019430 A1 * | 1/2004 | Hurban et al. ........... 702/19 |

FOREIGN PATENT DOCUMENTS

| JP | 2002-272708 A | * | 3/2001 |
| JP | 2003-061921 A | * | 8/2001 |
| JP | 2002-005827 A |   | 1/2002 |
| JP | 2002-328088 A |   | 11/2002 |

(Continued)

OTHER PUBLICATIONS

McCully et al., Impaired Oxygen Delivery to Muscle in Chronic Fatigue Syndrome, 1000, Clinical Science, vol. 97, pp. 603-608.*

(Continued)

*Primary Examiner* — James Kish
(74) *Attorney, Agent, or Firm* — Hogan Lovells US LLP

(57) ABSTRACT

The present invention provides a method and device of quantitatively or qualitatively examining and diagnosing chronic fatigue syndrome (CFS) by: irradiating a sample derived from an examinee or other animal with light having a wavelength in a range of 400 nm to 2500 nm or a wavelength in part of the range; detecting reflected light, transmitted light, or transmitted and reflected light to obtain an absorption spectral data; and analyzing absorbance at all measurement wavelengths or at specific wavelengths in the absorption spectral data by using an analytical model prepared beforehand.

15 Claims, 5 Drawing Sheets

FOREIGN PATENT DOCUMENTS

| | | |
|---|---|---|
| JP | 2005-055228 A | 3/2005 |
| WO | 01/75420 | 10/2001 |

OTHER PUBLICATIONS

Machine translation of JP2002-272708A, including cover page of the original.*

Machine translation of JP2003-061921A, including cover page of the original.*

McCully et al. Impaired Oxygen Delivery to Muscle in Chronic Fatigue Syndrome. 1999. Clincial Science. vol. 97, pp. 603-608.*

Tsukasa Sasaki, "Rodo Kagaku Kenkyusho ga Susumeru 'Mansei Hiro' Kenkyu", Digest of Science of Labour, [ISSN:0035-7774], vol. 60, No. 4, Apr. 1, 2005, pp. 32-35, and translation of relevant passage (left column of p. 34).

http://www.med.o saka-u. ac.jp/publbldonlwww/cfshome.html, and translation of relevant passage (written about "Tentative plan of CFS diagnostic criteria by Ministry of Health and Welfare, Mar. 1995").

Adler RH. Chronic fatigue syndrome (cfs)., Swiss Med Wkly. (2004) 134:268-76.

Akikazu Sakudo et al., "The diagnosis method using the analysis of near-infrared spectrophotometry", Sougourinsyo, Jan. 2006, vol. 55, No. 1, pp. 70-75.

JPO Office Action—Nov. 11, 2011.

English Translation—JPO Office Action—Nov. 11, 2011.

* cited by examiner

[Fig.1]
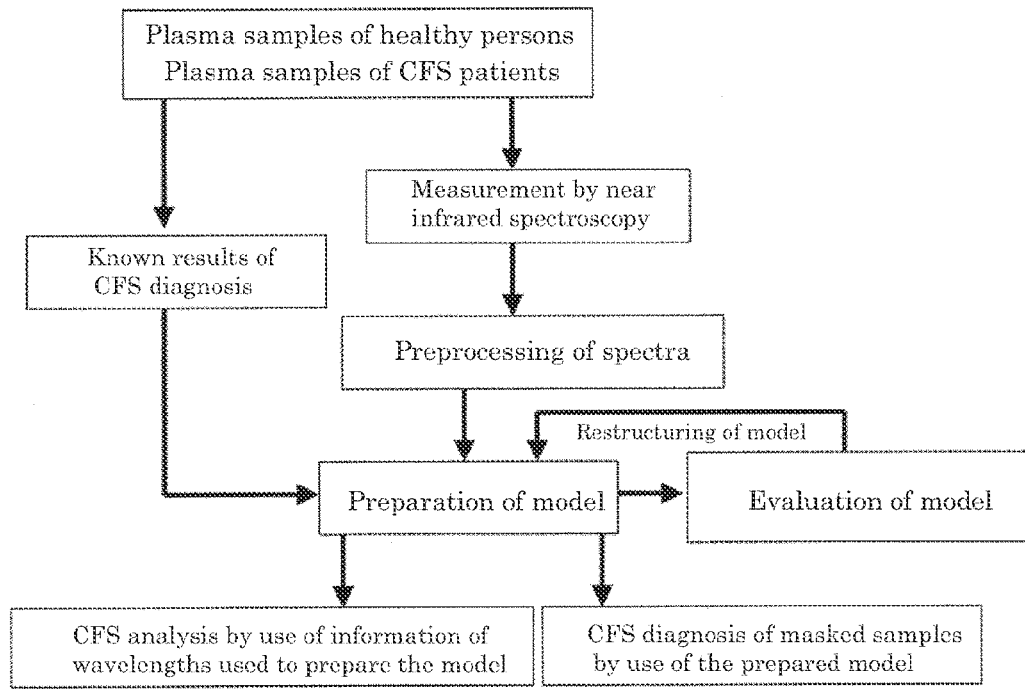
[Fig.2]
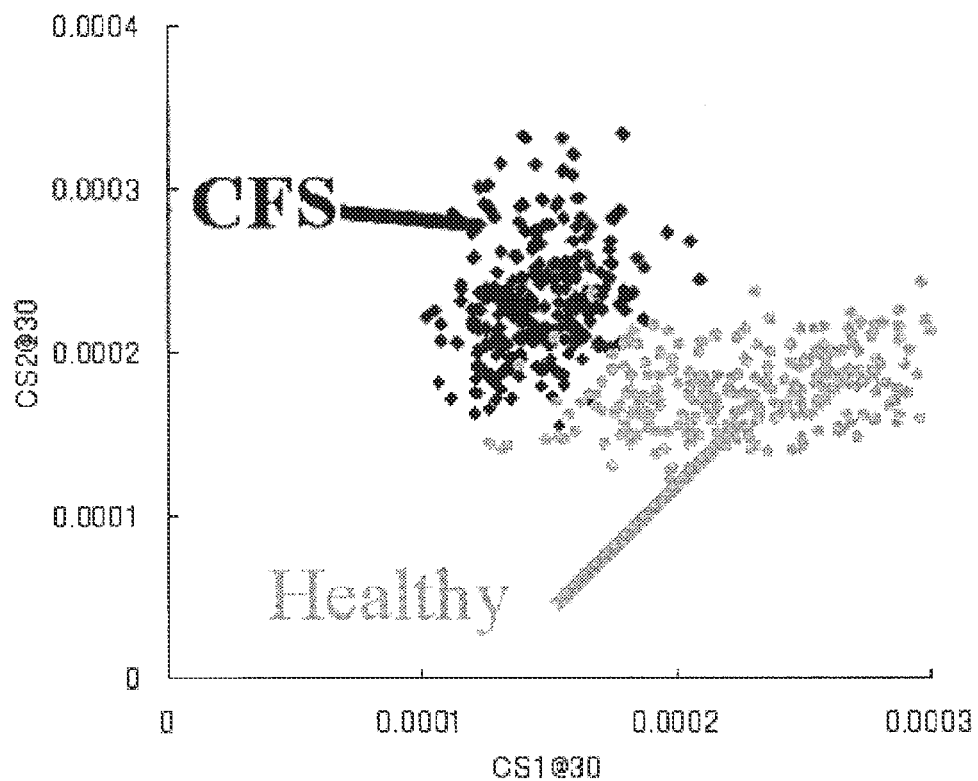

[Fig.3]
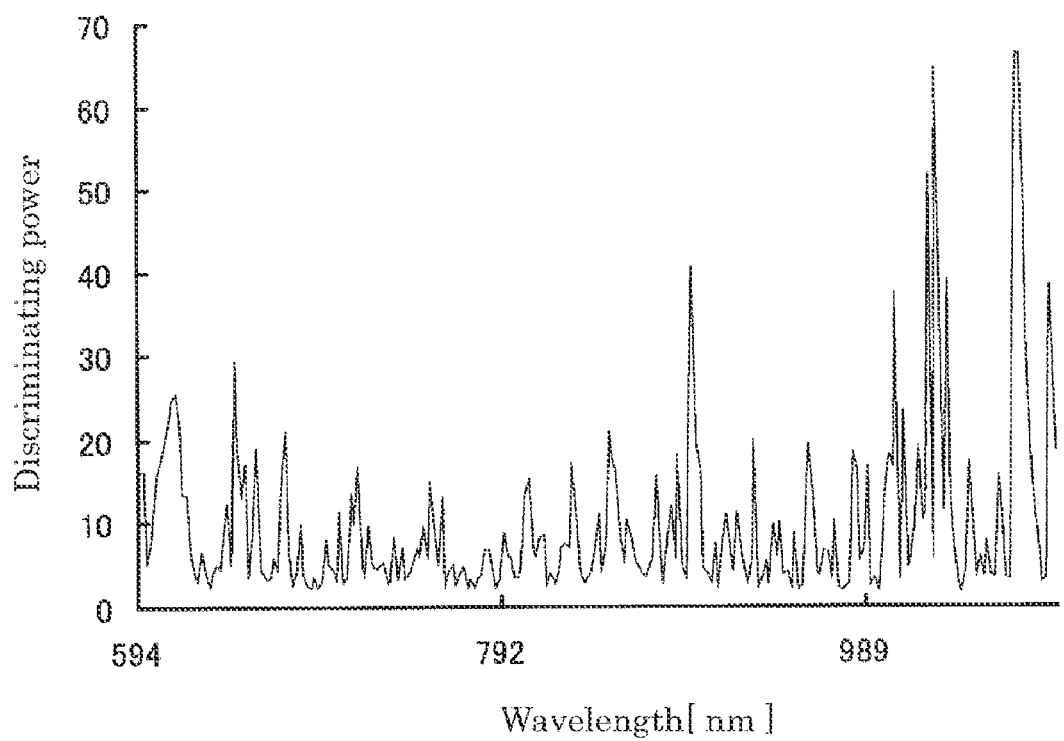

[Fig.4]
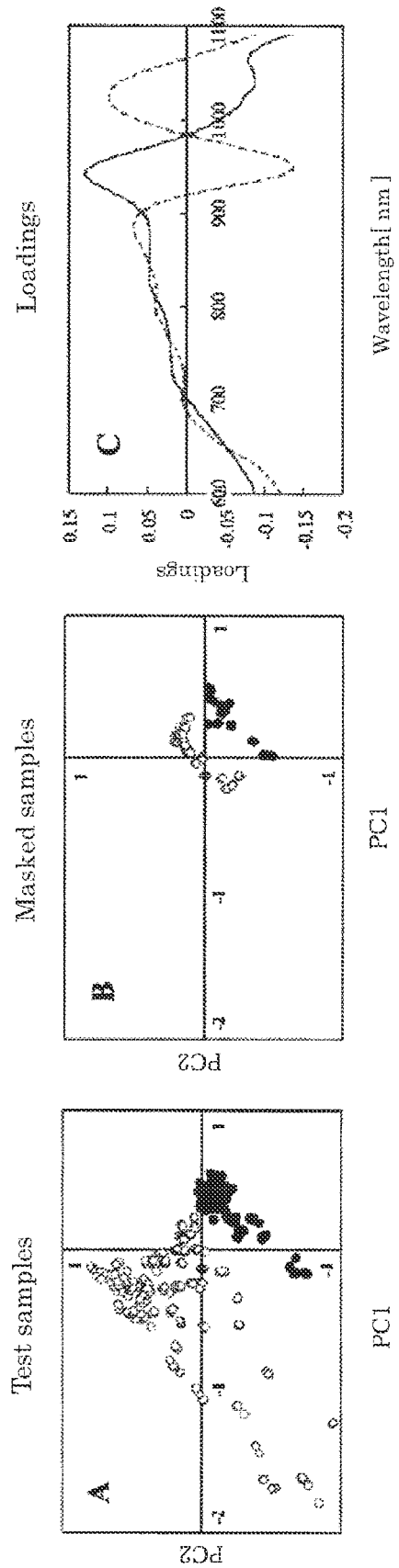

[Fig.5]
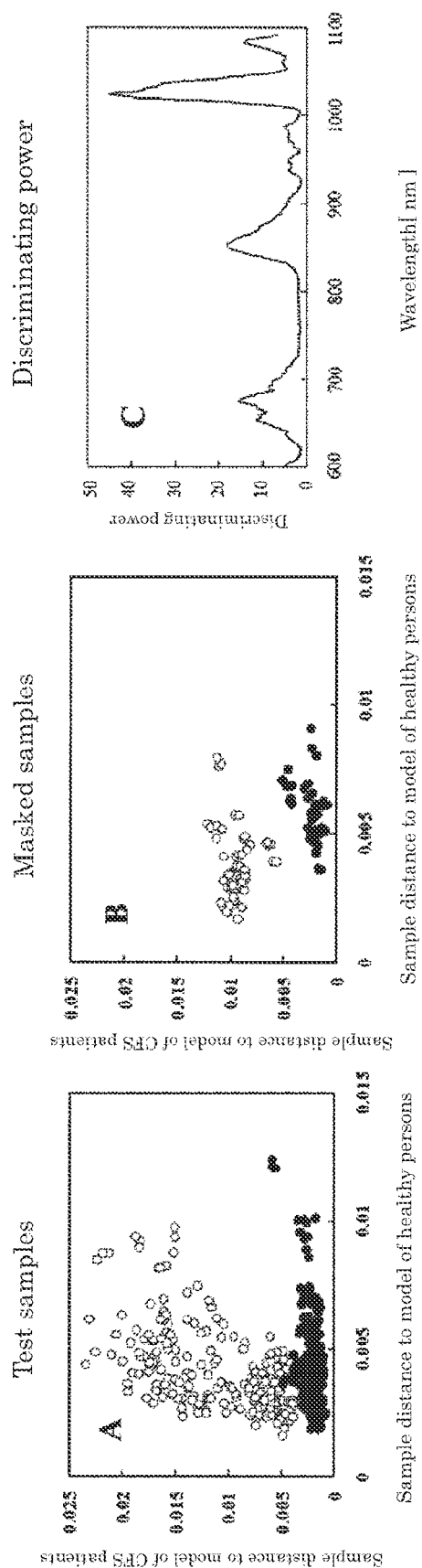

[Fig.6]
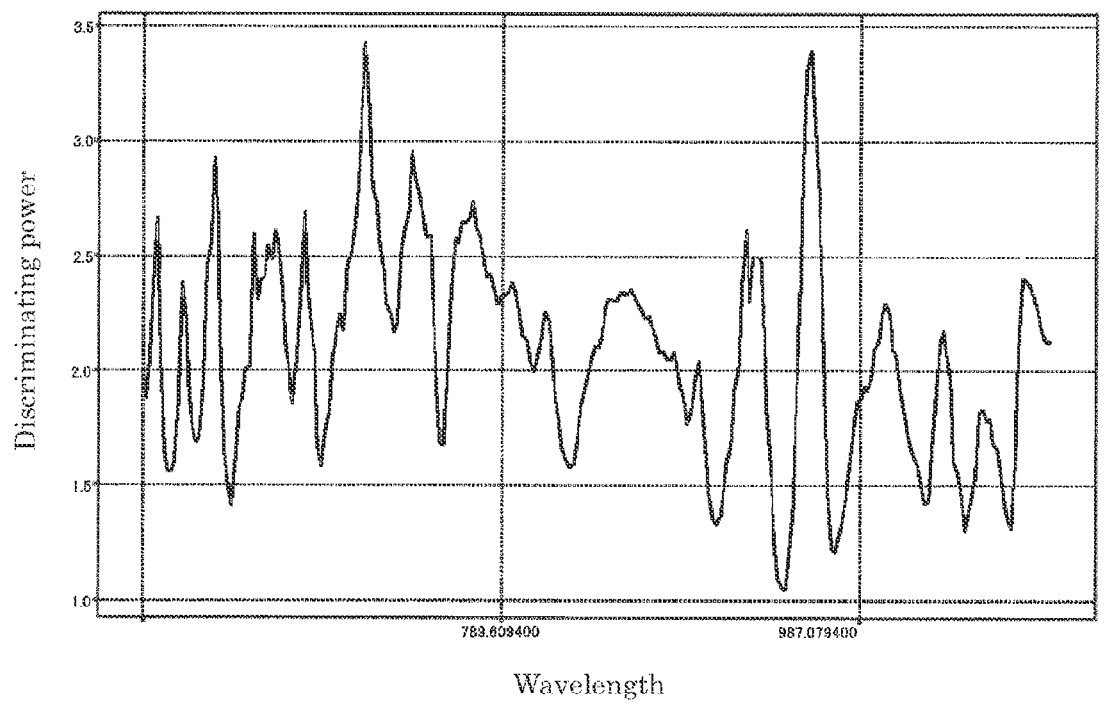
[Fig.7]
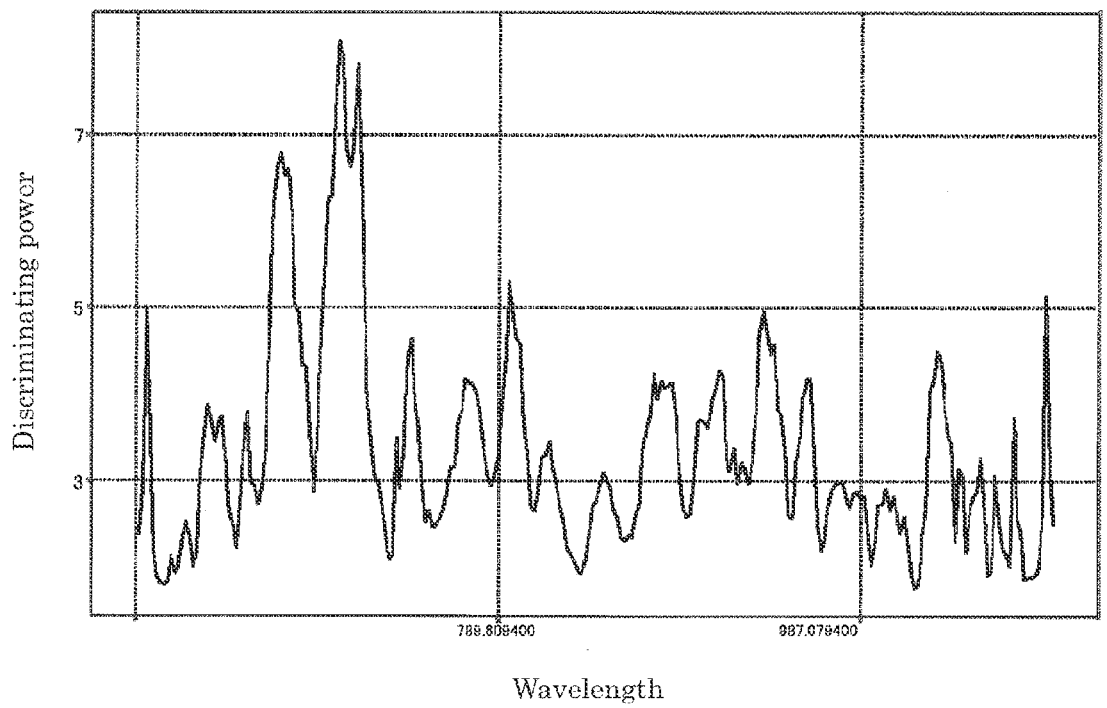

METHOD AND DEVICE FOR DIAGNOSING CHRONIC FATIGUE SYNDROME (CFS) BY USING NEAR INFRARED SPECTRUM

This application is the U.S. National Phase under 35 U.S.C. §371 of International Application PCT Patent Application No. PCT/JP2006/309656, filed on May 15, 2006, which claims priority to Japanese Patent Application No. 2005-146048, filed on May 18, 2005. The International Application was published under PCT Article 21(2) in a language other than English. The contents of which are all herein incorporated by this reference in their entireties. All publications, patents, patent applications, databases and other references cited in this application, all related applications referenced herein, and all references cited therein, are incorporated by reference in their entirety as if restated here in full and as if each individual publication, patent, patent application, database or other reference were specifically and individually indicated to be incorporated by reference.

TECHNICAL FIELD

The present invention relates to a method of examining and diagnosing chronic fatigue syndrome (CFS) by near infrared spectroscopy and a device that is used in that method.

BACKGROUND ART

Chronic fatigue syndrome (CFS) has been diagnosed on the basis of the clinical symptom. More specifically, the following symptoms of (1) and (2) are defined as major criteria in CFS diagnostic criteria made by Ministry of Health and Welfare (Nonpatent document 1 below).

(1) continuation of six months or more of such heavy fatigue condition that daily life is remarkably damaged, or repeated recurrence of such condition (such condition is seen in 50% or more of the period).

(2) the symptom is different from known physical disorders and mental depression, as a result of clinical history, physical findings and examination findings.

Moreover, the following criteria of symptoms and physical findings are defined as minor criteria in CFS diagnostic criteria made by Ministry of Health and Welfare.

A) criteria of symptoms (continuation of six months or more of the following symptoms, or repeated recurrence of such symptoms);

1. subfever (axillary temperature 37.2-38.3° C.) or chill, 2. pain in the throat, 3. swelling of cervical or axillary lymph nodes, 4. reduction of muscular power due to unclear reason, 5. pain or discomfort in the muscle, 6. continuation of 24 hours or more of feebleness of the whole body after light work, 7. pain in the head, 8. mobile pain in the joint without swelling and rubor accompanied, 9. psychiatric disorder (the following one or more); photophobia, transient scotoma, amnesia, irritability, confusion, thinking reduced, poor concentration, and depression, 10. sleep problem (excess or shortage of sleep), 11. the major symptoms appear in several hours to several days at the stage of development.

B) criteria of physical findings (two or more confirmations of the following physical findings by the doctor at the interval of at least one month or more);

1. subfever, 2. non-transudative inflammation in the throat, 3. swelling of cervical or axillary lymph nodes.

Thus, CFS diagnostic criteria are composed of two items of major criteria, and minor criteria (11 items of criteria of symptoms and 3 items of criteria of physical findings).

CFS has been diagnosed when the following requirements are satisfied; satisfaction of 8 items or more of criteria of symptoms (of minor criteria) in addition to two items of major criteria, or satisfaction of at least 6 items of criteria of symptoms and at least 2 items of criteria of physical findings, in addition to two items of major criteria. When two items of major criteria are satisfied, but the requirements are not satisfied in minor criteria, then it is evaluated "doubtful (pseudo) CFS." Among the CFS diagnosed by the above criteria, if the symptom of the CFS appeared following the infectious disease, then it is called "postinfectious CFS."

The above-mentioned CFS diagnostic method, however, depends on the clinical findings and opinions by the doctor. Therefore, more objective CFS diagnostic method is needed, which does not need skill and experience.

Currently, a component analysis using near infrared spectroscopy is being carried out in various fields. For example, a sample is irradiated with visible light and/or near-infrared rays, a wavelength range in which the visible light and/or near-infrared rays are absorbed by a specific component is detected, and the specific component is then analyzed quantitatively.

This is carried out as follows: for example, a sample is injected into a quartz cell, and this is irradiated with visible light and/or near-infrared rays in a wavelength range of 400 to 2500 nm, using a near-infrared spectroscope (such as an NIRSystem 6500 manufactured by Nireco Corp.); transmitted light, reflected light, or transmitted and reflected light is analyzed.

Generally, near-infrared rays have a very small absorbance coefficient to a substance, hardly undergo scattering, and are also a low-energy electromagnetic wave. Therefore they allow chemical/physical data to be obtained without damaging the sample.

Thus sample data can be obtained immediately by detecting, for example, transmitted light from a sample, determining the absorbance data of the sample, and subjecting this data to a multivariate analysis. For instance, the biomolecular structure or the process of change in its function can be obtained directly or in real time.

Examples of the conventional techniques relating to such near infrared spectroscopy include those described in patent documents 1 and 2 below. Patent document 1 discloses a method of obtaining data from a sample using visible and near-infrared rays, specifically, a method of discriminating the group to which an unknown sample belongs, a method of identifying an unknown sample, and a method of monitoring the time-dependent change in the sample in real time. This document does not disclose CFS diagnosis carried out by near infrared spectroscopy.

Patent document 2 discloses a method of diagnosing bovine mastitis by measuring a somatic cell in milk or the udder through a multivariate analysis of absorbance data obtained, using an absorption band of water molecules in the visible light and/or near-infrared region. Nonpatent document 2 discloses a clinical symptom of CFS and its mechanism considered.

[Nonpatent document 1] Tentative plan of CFS diagnostic criteria by Ministry of Health and Welfare, March, 1995.
[Nonpatent document 2] Adler R H. Chronic fatigue syndrome (CFS), Swiss Med Wkly. (2004) 134:268-76.
[Patent document 1] Japanese Laid-Open Patent Publication No. 2002-5827 (page 1-9, FIG. 1).

[Patent document 2] International Publication No. WO 01/75420 (page 1-5, FIG. 1).

DISCLOSURE OF INVENTION

As described above, there are demands for simple, quick, and highly accurate examination and diagnostic methods in CFS diagnosis. Particularly, when it is necessary to examine a large amount of samples at once, there are high demands for the development of a simple and quick examination method. Therefore the present invention is intended to provide a novel method and device for examining and diagnosing CFS simply, quickly, and with high accuracy, using a near-infrared spectroscopy.

As a result of analysis, the present inventors have clarified it is possible to examine and diagnose CFS by near infrared spectroscopy. Excellent examination and diagnosis of CFS can be realized by consideration of a method of measuring visible and near-infrared rays (VIS-NIR) spectra, a method of analyzing resultant spectral data, and a method of preparing an analytical model. These findings led to the present invention.

That is, the present invention embraces the following as medically and industrially useful inventions:

(A) A method of quantitatively or qualitatively examining and judging chronic fatigue syndrome (CFS), the method comprising:
   irradiating a sample derived from an examinee or other animal with light having a wavelength in a range of 400 nm to 2500 nm or a wavelength in part of the range,
   detecting reflected light, transmitted light, or transmitted and reflected light to obtain an absorption spectral data, and
   analyzing absorbance at all measurement wavelengths or at specific wavelengths in the absorption spectral data by using an analytical model prepared beforehand.

(B) The method according to item (A) described above, examining and judging chronic fatigue syndrome (CFS), by using a quantitative model prepared by a regression analysis, such as a PLS method.

(C) The method according to item (A) described above, examining and judging chronic fatigue syndrome (CFS), by using a qualitative model prepared by a class discriminant analysis, such as a SIMCA method.

(D) The method according to any one of items (A) to (C) described above, examining and judging chronic fatigue syndrome (CFS), by analysis of absorbance at two or more wavelengths selected from plural wavelength regions in a range of ±5 nm of each of wavelengths of 600-700 nm, 700-900 nm, 950-960 nm, 1020 nm and 1080 nm.

(E) The method according to any one of items (A) to (C) described above, examining and judging chronic fatigue syndrome (CFS), by analysis of absorbance at two or more wavelengths selected from plural wavelength regions in a range of ±5 nm of each of wavelengths of 650 nm, 670 nm, 700-715 nm, 740 nm, 850 nm, 950-960 nm, 1020 nm and 1080 nm.

(F) The method according to any one of items (A) to (E) described above, wherein the sample is blood (including blood plasma and serum), urine, another biological fluid, a tissue, a tissue extract, or a part of a living body such as an ear, or a fingertip of a hand or foot.

(G) An analytical model used for the method according to item (A) described above.

(H) The analytical model according to item (G) described above, analyzing absorbance at two or more wavelengths selected from plural wavelength regions in a range of ±5 nm of each of wavelengths of 600-700 nm, 700-900 nm, 950-960 nm, 1020 nm and 1080 nm.

(I) The analytical model according to item (G) described above, analyzing absorbance at two or more wavelengths selected from plural wavelength regions in a range of ±5 nm of each of wavelengths of 650 nm, 670 nm, 700-715 nm, 740 nm, 850 nm, 950-960 nm, 1020 nm and 1080 nm.

(J) A program for examination and diagnosis of chronic fatigue syndrome (CFS), making a computer carry out preparation and renewal of an analytical model used for the method according to item (A) described above, or examination and diagnosis by use of an analytical model prepared.

(K) A test and diagnostic device, comprising:
   a floodlight means for irradiating a sample derived from an examinee or other animal with light having a wavelength in a range of 400 nm to 2500 nm or a wavelength in part of the range,
   a spectroscopic means for carrying out spectroscopy before or after irradiation and a detection means for detecting reflected light, transmitted light, or transmitted and reflected light with respect to the light with which the sample was irradiated, and
   a data analysis means for quantitatively or qualitatively examining and diagnosing chronic fatigue syndrome (CFS), by analyzing absorbance at all measurement wavelengths or at specific wavelengths in an absorption spectral data obtained through the detection, by use of an analytical model prepared beforehand.

(L) The device according to item (K) described above, examining and diagnosing chronic fatigue syndrome (CFS), by using a quantitative model prepared by a regression analysis, such as a PLS method.

(M) The device according to item (K) described above, examining and diagnosing chronic fatigue syndrome (CFS), by using a qualitative model prepared by a class discriminant analysis, such as a SIMCA method.

(N) The device according to any one of items (K) to (M) described above, examining and diagnosing chronic fatigue syndrome (CFS), by analysis of absorbance at two or more wavelengths selected from plural wavelength regions in a range of ±5 nm of each of wavelengths of 600-700 nm, 700-900 nm, 950-960 nm, 1020 nm and 1080 nm.

(O) The device according to any one of items (K) to (M) described above, examining and diagnosing chronic fatigue syndrome (CFS), by analysis of absorbance at two or more wavelengths selected from plural wavelength regions in a range of ±5 nm of each of wavelengths of 650 nm, 670 nm, 700-715 nm, 740 nm, 850 nm, 950-960 nm, 1020 nm and 1080 nm.

(P) The device according to any one of items (K) to (O) described above, wherein the sample is blood (including blood plasma and serum), urine, another biological fluid, a tissue, a tissue extract, or a part of a living body such as an ear, or a fingertip of a hand or foot.

EFFECT OF THE INVENTION

The present invention realizes simple, quick and objective examination and judgment of CFS with high accuracy. Since the present invention realizes simple and quick examination, it is especially useful when a large amount of samples have to be examined at once. The present invention allows CFS test to be carried out by using a sample derived from blood, such as plasma or serum. Examples of the sample to be used can include urine, another biological fluid, and a part of a living body such as an ear, or a fingertip of a hand or foot. Thus the present invention realizes non-invasive examination without damaging a living body.

BRIEF DESCRIPTION OF DRAWINGS

FIG. 1 is a view for explaining a method of preparing an analytical model, and examination and diagnosis of CFS by the prepared analytical model in the present invention.

FIG. 2 is a graph showing a Coomans plot obtained by a SIMCA analysis of samples, each of which was five fold diluted, in the CFS examination in the example 1 of the present invention.

FIG. 3 is a graph showing the discriminating power (vertical axis) at each wavelength (horizontal axis) that was obtained by the SIMCA analysis, in the CFS examination in the example 1 of the present invention.

FIG. 4 shows a result of examination and diagnosis by use of an analytical model (PCA model) obtained by the PCA, in the CFS examination in the example 2 of the present invention. In graph A, the PCA score of test samples is plotted to the first principal component (PC1) axis and the second principal component (PC2) axis. In graph B, the PCA score of masked samples is plotted to the PC1 axis and the PC2 axis. In the graphs A and B, open circle (○) represents healthy donor sample whereas closed circle (●) represents CFS patient sample. Graph C shows the loadings of PC1 (solid line) and PC2 (broken line) in the PCA model.

FIG. 5 shows a result of examination and diagnosis by use of an analytical model (SIMCA model) obtained by the SIMCA method, in the CFS examination in the example 2 of the present invention. Graph A is a Coomans Plot, showing excellent classification of test samples between healthy donor group (○) and CFS patient group (●). Graph B is a Coomans Plot, showing excellent discrimination and prediction of masked samples between healthy donor group (○) and CFS patient group (●). Graph C shows discriminating power at each wavelength of the SIMCA model.

FIG. 6 is a graph showing the discriminating power (vertical axis) at each wavelength (horizontal axis) in the SIMCA model obtained as a result of the SIMCA analysis (Factor10), in the CFS examination in the example 3 of the present invention.

FIG. 7 is a graph showing the discriminating power (vertical axis) at each wavelength (horizontal axis) in the SIMCA model obtained as a result of the SIMCA analysis (Factor20), in the CFS examination in the example 3 of the present invention.

DESCRIPTION OF THE PREFERRED EMBODIMENTS

Hereinafter, a device (hereinafter referred to as "the device") for quantitatively or qualitatively examining and diagnosing CFS is described as an embodiment of the present invention with reference to the drawings.

[1] VIS-NIR Spectrum Measurement and Data Analytical Methods Using the Device

[1.1] Outline of VIS-NIR Spectrum Measurement

For the examination and diagnosis to be carried out with the device, a method of the present invention is employed. That is, CFS is examined and judged quantitatively or qualitatively by (a) irradiating a sample derived from an examinee or other animal with light having a wavelength in a range of 400 nm to 2500 nm or in part of the range; (b) detecting reflected light, transmitted light, or transmitted and reflected light to obtain absorption spectral data; and (c) analyzing absorbance at all measurement wavelengths or at specific wavelengths in the absorption spectral data by using an analytical model prepared beforehand.

A first feature point of the device resides in performing CFS diagnosis simply and quickly with high accuracy. The wavelength of light with which the sample is irradiated is in the range of 400 nm to 2500 nm or in part of the range (for example, 600 to 1000 nm). This wavelength range can be set as one wavelength region or as a plurality of regions, which include a light wavelength required for examination and judgment to be carried out with a used analytical model which has been prepared beforehand.

The light source to be used is, for example, a halogen lamp or an LED, but is not particularly limited. The sample is irradiated with light emitted from the light source directly or through a floodlight means such as a fiber probe. As described later, a pre- or postspectroscopy method can be employed. In the prespectroscopy method, the components of light are separated with a spectroscope before the sample is irradiated with it. In the postspectroscopy method, the components of light are separated after the sample is irradiated with it. With respect to the prespectroscopy method, there are two methods, including one of separating components of light emitted from a light source with a prism at the same time, and a method of changing the wavelength continuously by changing the slit space of a diffraction grating. In the latter method, the light emitted from the light source is decomposed at predetermined wavelength intervals, and thereby the sample is irradiated with continuous-wavelength light whose wavelength is changed continuously. In the examples described later, light with a wavelength in the range of 600 to 1000 nm is decomposed at a wavelength resolution of 2 nm, and the sample is irradiated with light whose wavelength is changed continuously in increments of 2 nm.

In regard to the light with which the sample was irradiated, reflected light, transmitted light, or transmitted and reflected light is detected by a detector, and raw absorption spectral data can thereby be obtained. Examination and judgment can be carried out with the analytical model by using the raw absorption spectral data without further processing. However, preferably, after a data conversion process in which a peak in the spectra obtained above is decomposed into component peaks by a spectroscopic method or multivariate analysis method is carried out, the examination and judgment proceeds with the analytical model by using the converted absorption spectral data. Examples of the spectroscopic method include secondary differential processing and Fourier transformation. On the other hand, examples of the multivariate analysis technique include wavelet conversion and a neural network technique. They are not particularly limited, however.

[1.2] Data Analysis Method (Preparation of Analytical Model)

The device examines and diagnoses CFS by analyzing absorbance at specific wavelengths (or at all measurement wavelengths) of the absorption spectral data obtained as described above, with the analytical model. That is, in order to perform final examination and diagnosis, we must prepare the analytical model beforehand. However, this analytical model can also be prepared when the spectra are measured.

In other words, it is desirable that the analytical model be prepared before the measurement. The examination and diagnosis, however, can be carried out by dividing the spectral data obtained at the time of the measurement into two, i.e., data for preparing the analytical model and for examination and diagnosis, and using an analytical model obtained based on the data for preparing it. For instance, when a large amount of samples are to be examined at once, a part of samples are used for preparing the analytical model. In this case, the analytical model is therefore prepared at the time of the measurement. In this method, the analytical model can be prepared without requiring teacher data, and this technique is applicable to both the quantitative and qualitative models.

The analytical model can be prepared by the multivariate analysis. For example, when the degree of fatigue (degree or progress of symptom) is to be estimated for the CFS test, a data matrix that stores absorption spectra at all wavelengths obtained by the spectral measurement is decomposed into a score matrix and a loading matrix by singular value decomposition. Then the principal component that summarizes the variation in the degree of fatigue in the sample is extracted (principal component analysis). This allows an independent component with low colinearity (=high correlation between predictor variables) to be used for the multiple linear regression analysis. A multiple linear regression analysis using the predictor variable as score and the dependent variable as the degree of fatigue is then employed. This makes it possible to prepare the analytical model that is used for estimating the degree of fatigue from the absorption spectra at all the measurement wavelengths or at specific wavelengths. These operations of series (multivariate analyses) have been established as a principal component regression (PCR) or a partial least squares (PLS) regression method (reference: Multivariate Analysis for Chemists—Introduction to Chemometrics, Yukihiro Ozaki, Akifumi Uda, Toshio Akai; published by Kodansha, 2002). Examples of the regression analysis include a classical least squares (CLS) method and a cross-validation method in addition to the above.

Although the above-mentioned methods are used for preparing a quantitative analytical model, the multivariate analysis can be used for preparing the qualitative analytical model. Examples of the multivariate analysis include a principal component analysis (PCA), a soft independent modeling of class analogy (SIMCA) method, and a k nearest neighbors (KNN) method for class discrimination. In the SIMCA method, the respective principal components of a plurality of groups (classes) are analyzed, and the principal component model of each class is prepared. Then an unknown sample is compared to the principal component model of each class and is assigned to the class of the principal component model that it best matches. Moreover, the class discrimination analysis, such as the SIMCA method, can be said to be a method of classifying absorption spectra or regression vectors into respective classes through pattern recognition.

Preparation of the analytical model using a multivariate analysis such as the SIMCA method or PLS method can be carried out by using self-produced software or commercial multivariate analysis software. Furthermore, the production of software specialized for an intended use (that is, program for examination and diagnosis of CFS) allows quick analysis to be carried out.

An analytical model assembled using such multivariate analysis software is stored as a file. The file is retrieved in examining and diagnosing an unknown sample, and quantitative or qualitative examination and diagnosis is then carried out, using the analytical model with respect to the unknown sample. This makes it possible to carry out a simple and quick examination and diagnosis of CFS. With respect to the analytical model, it is preferable that a plurality of analytical models such as a quantitative model and a qualitative model be stored as files and that the respective models be updated suitably.

Thus, the program (analytical software) for examination and diagnosis of the present invention makes a computer carry out production and renewal of an analytical model, or examination and diagnosis concerning CFS based on the spectral data of a sample by use of the prepared analytical model. The program of the present invention can be provided as a recording medium in which the program can be read with a computer. Examples of such recording medium include a flexible disk, a hard disk, a magnetic memory medium such as a magnetic tape, an optical memory medium such as CD-ROM, CD-R, CD-RW, DVD-ROM, DVD-RAM and DVD-RW, an electric memory medium such as RAM and ROM, and a magnetic/optical memory medium such as MO.

Once the analytical model is prepared, the light with a wavelength required for the examination and diagnosis to be carried out using the analytical model is determined. The device can have a simpler configuration by allowing a sample to be irradiated with light with one or a plurality of the wavelength regions determined above.

As shown in the Examples described later, it is preferable, as a result of analysis, to examine and judge chronic fatigue syndrome (CFS), by analysis of absorbance at two or more wavelengths (more preferably about 2-15 or 2-10 wavelengths) selected from plural wavelength regions in a range of ±5 nm of each of wavelengths of 600-700 nm (preferably 650 nm and 670 nm), 700-900 nm (preferably 700-715 nm, 740 nm and 850 nm), 950-960 nm, 1020 nm and 1080 nm, since these wavelengths were found to be effective for examination and diagnosis of CFS. Also, it is preferable to prepare an analytical model by using absorbance at the above-mentioned wavelengths.

The summary of the above-mentioned step of preparing an analytical model and step of examining and diagnosing CFS by the prepared analytical model is shown in FIG. 1. For example, in the step of preparing an analytical model, measurement is done by near infrared spectroscopy to plasma samples of healthy persons as well as plasma samples of CFS patients, followed preprocessing of obtained spectral data. Then, multivariate analysis is done in reference to known results of CFS diagnosis, to prepare an analytical model. The prepared analytical model can be evaluated by examining and diagnosing CFS by use of masked samples, or by examination and diagnosis of CFS including data (information of wavelengths) used to prepare the analytical model. It is preferable to restructure the prepared analytical model by updating it, if more evaluated analytical model is obtained.

[2] Specific Configuration of the Device

An examination and diagnosis system of the device can be configured with four components, (i) a probe (floodlight part), (ii) a spectroscope and detection unit, (iii) a data analysis unit, and (iv) a result display unit. The respective components are described below.

[2.1] Probe (Floodlight Means)

The probe has a function of guiding light (in the whole wavelength range of 400 nm to 2500 nm or in part of the range) emitted from a light source, such as a halogen lamp or an LED, to a sample, a measurement target. For instance, the probe can be a fiber probe and have a configuration in which light is cast over a measurement target (sample) through a flexible optical fiber. Generally, a probe for a near-infrared spectroscope can be produced inexpensively and thus is low in cost.

The device can have a configuration in which light emitted from a light source is cast directly over a sample, a measurement target. In that case the probe is not necessary and the light source serves as a floodlight means.

As described above, once an analytical model is prepared, the light wavelength required for the examination and diagnosis to be carried out using the analytical model is determined. The device can have a simplified configuration by employing a configuration in which a sample is irradiated with light in one or more of the wavelength regions determined above.

[2.2] Spectroscope and Detection Unit (Spectroscopic Means and Detection Means)

The device has a configuration of a near-infrared spectroscope as a measurement system. Generally, the near-infrared spectroscope allows a measurement target to be irradiated with light and detects, in a detection unit, reflected light, transmitted light, or transmitted and reflected light with respect to the target. Furthermore, in regard to the light thus detected, the absorbance with respect to incident light is measured at each wavelength.

A spectroscopic system includes pre- and postspectroscopy. In prespectroscopy, light is separated into its spectral components before being cast over a measurement target. In postspectroscopy, light from the measurement target is separated into its spectral components and detected. The spectroscope and detection unit of the device can employ either prespectroscopy or postspectroscopy as a spectroscopic system.

There are three types of detection methods, a reflected light detection, a transmitted light detection, and a transmitted and reflected light detection. In the reflected light detection and transmitted light detection, light reflected from and light transmitted through a measurement target each are detected by a detector. In the case of the transmitted and reflected light detection, a detector detects light that has entered a measurement target to become a refracted light, which is reflected inside the target and is then again emitted outside the target. The spectroscope and detection unit of the device can employ any one of the reflected light detections, transmitted light detections, and transmitted and reflected light detections as a detection system.

The detector in the spectroscope and detection unit can be formed, for example, of a charge coupled device (CCD), which is a semiconductor device, but is not limited to this. Another photodetector can be used for the detector. The spectroscope also can be formed by a known method.

[2.3] Data Analysis Unit (Data Analysis Means)

Absorbance at each wavelength, i.e., absorption spectral data, is obtained from the spectroscope and detection unit. The data analysis unit carries out a CFS diagnosis based on the absorption spectral data by using an analytical model prepared beforehand as described above.

In regard to the analytical model, it is preferable to prepare a plurality of analytical models, including a quantitative model and a qualitative model, and to use a suitable one according to the type of evaluation, to be carried out, i.e., a quantitative evaluation or a qualitative evaluation.

Data analysis unit can be formed of: a storage unit for storing various data, such as spectral data, programs for a multivariate analysis, and analytical models, and an operation unit that carries out arithmetic processing based on these data and programs. Data analysis unit can be formed, for example, of an IC chip. Therefore the device can be easily reduced in size so as to be a portable type. The above-mentioned analytical models can be stored in the storage unit, such as an IC chip.

[2.4] Result Display Unit (Display Means)

Result display unit displays analytical results obtained in the data analysis unit. Specifically, it displays the result, such as the degree of fatigue, obtained as a result of the analysis carried out with an analytical model. In the case of a qualitative model, it displays, for example, "CFS", "High possibility of CFS", "Low possibility of CFS", "High degree of fatigue", "Low degree of fatigue" and "Healthy", according to the class discrimination results. In the case where the device is of a portable type, the result display unit is preferably a flat display formed, for example, of liquid crystal.

As mentioned above, the device can be used for examination and diagnosis of CFS. Here, examination and diagnosis of CFS include various kinds of examination and diagnosis of CFS, such as examination and diagnosis of a degree of fatigue (degree of diseased fatigue), a quantitative evaluation of progress of CFS, an evaluation and judgment of CFS risk.

EXAMPLES

Examples of the present invention are described below, but do not limit the present invention. The examples show examination and diagnosis of CFS can be realized by near infrared spectroscopy.

Example 1

[1.1] Measurement of Absorption Spectrum

In this example, the absorption spectra of each sample were measured by the following measurement method.

With respect to a total of 211 specimens, including 119 of normal donor plasma and 92 of CFS patients plasma, their concentrations each were diluted with a PBS by five times, and these diluted plasma samples were used as samples.

1 mL of each sample was placed in a polystyrene cuvette and measurement was then carried out, with a near infrared spectroscopic system (trade name: FQA-NIRGUN, Japan Fantec Research Institute, Shizuoka Japan). Specifically, the sample was irradiated three times consecutively with light having a wavelength of 600 to 1000 nm, and absorption spectra were measured by detecting each reflected light. The wavelength resolution was 2 nm. The length of the optical path that passes through the sample was set at 10 mm.

[1.2] Analysis of Absorption Spectrum

In this example, the resultant absorption spectra were subjected to multivariate analysis by the SIMCA method, in order to prepare an analytical model. Known results of CFS diagnosis were determined beforehand according to CFS diagnostic criteria made by Ministry of Health and Welfare. In the classification of this SIMCA method, CFS patients were defined as class 1 and healthy persons were defined as class 2.

In this example, a commercial software for a multivariate analysis (Pirouette ver. 3.01 (trade name), Informetrics) was used for preparing an analytical model, and the SIMCA analysis was carried out with the algorithm shown in Table 1 below. 191 specimens, including 109 samples of normal donor plasma and 82 samples of CFS patients plasma, were used for preparing an analytical model by this SIMCA analysis. The utility to CFS diagnosis was evaluated whether or not 10 samples of normal donor plasma and 10 samples of CFS patients plasma (these samples were not used for preparing an analytical model) can be diagnosed correctly by the prepared analytical model.

TABLE 1

| SIMCA | |
|---|---|
| # of Included Samples: | 573 |
| Preprocessing: | Mean-center |
| Scope: | Local |
| Maximum factors: | 30 |
| Optimal factors: | 30, 30 |
| Prob. threshold: | 0.9500 |
| Calib Transfer: | Not enabled |
| Transforms: | |
| SNV | |
| Smooth(25) | |

Brief descriptions of the above-mentioned algorithms follow. The "number of included samples" denotes the number of samples used for analysis (the number of spectra). The number of samples, 573, denotes that three absorption data obtained through three-time consecutive irradiations, respectively, were used per sample.

"Preprocessing" denotes a preliminary treatment, and "Mean-center" denotes the use of a method in which the starting point of a plot was moved to the center of data set. For "Scope", there are global and local types. In this case, the local type was selected. The item "Maximum factors" denotes the number of factors (main component) to be analyzed to the maximum, and 30 was selected as Maximum factors. The term "Optimal factors" indicates the number of factors that were most suitable for preparing an analytical model as a result of analysis, and "30, 30" denotes that the most suitable number of factors in Class 1 is up to 30, and the most suitable number of factors in Class 2 is up to 30. "Probability threshold" means the threshold in judging whether it belongs to a certain class. "Calibration transfer" denotes whether mathematical adjustment is carried out for reducing the difference between devices. "Transform" means conversion, and "smooth" denotes that smoothing was carried out. The conversion of smoothing denotes that based on the principle of a Savitzky-Golay polynomial filter, convolution to the predictor variable in a window, including a point of central data and n points on one side, was carried out, and n=25 was selected. SNV is a method of amending the dispersion. First, the standard deviation and the average of variables of samples are calculated. Next, the mean is pulled from each variable value and then, the value is amended by dividing by the standard deviation.

FIG. 2 shows a Coomans plot obtained as a result of the SIMCA analysis of this example. Table 2 indicates the results of Interclass distances, and Table 3 indicates the results of Misclassification.

TABLE 2

| | CS1@30 | CS2@30 |
|---|---|---|
| CS1 | 0.0000 | 1.9472 |
| CS2 | 1.9472 | 0.0000 |

In Table 2, CS1 and CS2 denote Class 1 and Class 2, respectively (hereinafter, the same applies). Furthermore, CS1@30 means that 30 factors (main components) are used in Class 1. The same applies below, and the number described after "@" denotes the number of factors that were used.

TABLE 3

| | Pred1@30 | Pred2@30 | No match |
|---|---|---|---|
| Actual1 | 245.0000 | 1.0000 | 0.0000 |
| Actual2 | 27.0000 | 300.0000 | 0.0000 |

In Table 3, "Actual 1" denotes that the actual class is "1", and the same applies to the others. Furthermore, "Pred1" means that the class estimated using an analytical model obtained by the SIMCA analysis is "1", and the same applies to the others. "No match" denotes the case where the sample was neither judged CFS nor healthy is indicated by numerical values. As shown in these results, it was possible to excellently discriminate between CFS and healthy by the analytical model obtained by the SIMCA analysis.

Next, masked samples, which were excluded from use for preparation of the model, were examined and diagnosed by using the analytical model obtained by the SIMCA analysis. Table 4 listed below shows the result.

TABLE 4

| | All samples | | | | Excluded samples | | |
|---|---|---|---|---|---|---|---|
| | Pred1 | Pred2 | No match | | Pred1 | Pred2 | No match |
| Actual1 | 266 | 8 | 0 | Actual1 | 23 | 7 | 0 |
| Actual2 | 20 | 332 | 5 | Actual2 | 1 | 24 | 5 |

In Table 4, "Actual 1" denotes that the actual class is "1", and the same applies to the others. Furthermore, "Pred1" means that the class estimated using an analytical model obtained by the SIMCA analysis is "1", and the same applies to the others. "No match" denotes the case where the sample was neither judged as CFS nor as healthy. All Samples are results of prediction of not only masked samples but also the samples used for preparation of the model. Excluded samples are results of prediction of only masked samples. As shown in Table 4, it was possible to excellently diagnose CFS of masked samples.

FIG. 3 shows discriminating power (vertical axis) at each wavelength (horizontal axis) obtained as a result of the SIMCA analysis. At the wavelengths at which the value of the discriminating power is higher, the difference in the two classes increases. That is, it is considered that the sharp peak wavelength at which the discriminating power is high is one of the effective wavelengths for discriminating between normal donor blood plasma and CFS patient blood plasma. Accordingly, CFS can be diagnosed simply and quickly with high accuracy by carrying out discrimination, with attention being focused on the wavelengths obtained by the SIMCA analysis, as described above.

The analytical model thus prepared is stored as a file, which is retrieved when an unknown sample is to be examined and diagnosed, and the classification of the unknown sample is estimated by using the analytical model. This allows CFS to be examined and diagnosed simply and quickly.

Example 2

In this example, the absorption spectra of each sample were measured by the following measurement method. With respect to a total of 148 specimens, including 71 samples of normal donor sera and 77 samples of CFS patients sera, their concentrations each were diluted with a PBS by ten times, and these diluted sera samples were used as test samples, for preparation of each analytical model for CFS diagnosis by PCA (principal component analysis) and SIMCA method. Moreover, 99 masked samples (CFS patients group 45 and Healthy donors group 54) were evaluated whether or not these samples were able to be correctly diagnosed by each analytical model.

With respect to absorbance measurement of each sample, 2 mL of each sample was placed in a polystyrene cuvette and measurement was then carried out, with a near infrared spectroscopic system (FQA-NIRGUN). Specifically, the sample was irradiated three times consecutively with light having a wavelength of 600 to 1100 nm, and absorption spectra were measured by detecting each reflected light. The wavelength resolution was 2 nm. The temperature of the measurement was set at 37° C.

In this example, multivariate analyses based on PCA and SIMCA method were carried out to absorption spectra obtained by the above method, for preparation of each analytical model. Commercial software (Pirouette ver. 3.11 (trade name), Informetrics) was used for preparing each analytical model.

FIG. 4 shows results of examination and diagnosis of CFS by use of the analytical model (PCA model) obtained by the PCA. Graph A is a result where the PCA score of each test sample is plotted to the first principal component (PC1) axis and the second principal component (PC2) axis. Graph B is a result where the PCA score of each masked sample is plotted to the PC1 axis and the PC2 axis. In the graphs A and B, open circle (○) represents healthy donor sample whereas closed circle (●) represents CFS patient sample. Graph C shows the loadings of PC1 (solid line) and PC2 (broken line) in the PCA model.

As shown in graph A, test samples were excellently discriminated between healthy donor sera and CFS patient sera by the PCA score using the PC1 and PC2. Moreover, as shown in graph B, masked samples were correctly discriminated between healthy donor sera and CFS patient sera by the PCA model. This result shows the PCA model is useful for CFS diagnosis.

FIG. 5 shows results of examination and diagnosis of CFS by use of the analytical model (SIMCA model) obtained by the SIMCA method. Graph A is a Coomans Plot, showing excellent classification of test samples between healthy donor sera (○) and CFS patient sera (●). Graph B is a Coomans Plot, showing excellent discrimination and prediction of masked samples between healthy donor sera (○) and CFS patient sera (●). Graph C shows discriminating power at each wavelength of the SIMCA model.

More specifically, with respect to the classification of test samples by the SIMCA model, 209 of 213 samples of healthy donor group (98.1%) and 220 of 231 samples of the CFS patient group (95.2%) were correctly discriminated by the SIMCA model. The number of samples includes each absorbance data obtained by consecutive three irradiations. With respect to the classification of masked samples by the SIMCA model, 54 of 54 samples of healthy donor group (100%) and 42 of 45 samples of the CFS patient group (93.3%) were correctly discriminated and predicted by the SIMCA model. Thus, the SIMCA model was useful for CFS diagnosis.

The important wavelengths in the above PCA model can be determined according to information of the loadings. As for the first principal component (PC1), a positive peak of the loadings was around 950 nm, while a negative peak was around 1020 nm, as shown in graph C of FIG. 4. Moreover, the loadings were lower around 600-700 nm and higher around 700-900 nm. As for the second principal component (PC2), a negative peak of the loadings was around 950 nm, while a positive peak was around 1020 nm. Moreover, the loadings were lower around 600-700 nm and higher around 700-900 nm.

The wavelengths important for discrimination in the above SIMCA model can be determined according to discriminating power. The values of discriminating power in the SIMCA model were higher around 650, 850, 1020 and 1080 nm, as shown in graph C of FIG. 5.

From the above results, simple, quick and accurate CFS diagnosis can be realized by each analytical model prepared by the PCA and SIMCA methods, on the basis of absorption spectrum data of serum sample obtained by near infrared spectroscopy. Moreover, this method may be used for not only the CFS diagnosis but also the discovery of unknown molecular marker in the blood (the causative agent of CFS), through the analysis of wavelengths important for discrimination, in addition to the CFS diagnosis with the marker, the research of the CFS disease mechanism, and the development of CFS therapy.

Example 3

In this example, the finger was employed as a subject, that is, spectral data was obtained from the tip of a finger in a non-invasive manner, and CFS diagnosis was carried out by an analytical model prepared the SIMCA method on the basis of the spectral data. More specifically, with respect to 92 persons (42 CFS patients and 50 healthy persons), transmission light from the finger of each person was measured three times by near infrared spectroscopy. Then, it was examined whether the analytical model for CFS diagnosis can be prepared by the SIMCA analysis to the obtained spectral data.

In this example, the same software as the example 2 was used for preparation of the analytical model, and the SIMCA analysis was carried out by the algorithm shown in Table 5 below. Note that the algorithm listed below shows the case where the number of Factors was set as 20, but this example also includes the case where the number of Factors was set as 10. In the classification of the SIMCA analysis, healthy donors were defined as class 1 and CFS patients were defined as class 2.

TABLE 5

| SIMCA | |
|---|---|
| # of Included Samples: | 276 |
| # of Included X vars: | 253 |
| Class Variable: | CFS(healthy = 1 CFS = 2) |
| Preprocessing: | Mean-center |
| Scope: | Local |
| Maximum factors: | 20 |
| Optimal factors: | 20, 20 |
| Prob. threshold: | 0.9500 |
| Calib Transfer: | Not enabled |
| Transforms: | |
| Smooth(17) | |

Tables 6 and 7 below are results of the case where the number of Factors was set as 10. Table 6 shows the result of the interclass distance while Table 7 shows the result of the misclassification. As shown in these results, samples were excellently discriminated between CFS and healthy, by the analytical model prepared by this SIMCA analysis and thus, CFS diagnosis can be realized by the analytical model.

TABLE 6

|  | CS1@10 | CS2@10 |
| --- | --- | --- |
| CS1 | 0 | 0.340515 |
| CS2 | 0.340515 | 0 |

TABLE 7

|  | Pred1@10 | Pred2@10 | No match |
| --- | --- | --- | --- |
| Actual1 | 134 | 16 | 0 |
| Actual2 | 18 | 107 | 1 |

FIG. 6 is a graph showing discriminating power at each wavelength in the SIMCA model obtained as a result of the SIMCA analysis (Factor10). As shown in this graph, the values of discriminating power in the SIMCA model were higher around 715, 740 and 960 nm.

Tables 8 and 9 below are results of the case where the number of Factors was set as 20. Table 8 shows the result of the interclass distance while Table 9 shows the result of the misclassification. As shown in these results, samples were excellently discriminated between CFS and healthy, by the analytical model prepared by this SIMCA analysis and thus, CFS diagnosis can be realized by the analytical model.

TABLE 8

|  | CS1@20 | CS2@20 |
| --- | --- | --- |
| CS1 | 0 | 0.664288 |
| CS2 | 0.664288 | 0 |

TABLE 9

|  | Pred1@20 | Pred2@20 | No match |
| --- | --- | --- | --- |
| Actual1 | 147 | 3 | 0 |
| Actual2 | 6 | 120 | 0 |

FIG. 7 is a graph showing discriminating power at each wavelength in the SIMCA model obtained as a result of the SIMCA analysis (Factor20). As shown in this graph, the values of discriminating power in the SIMCA model were higher around 670, 700 and 710 nm.

INDUSTRIAL APPLICABILITY

As described above, the present invention allows chronic fatigue syndrome (CFS) to be examined and judged simply, quickly and objectively with high accuracy. Thus the present invention is widely applicable to examination and diagnosis of CFS.

The invention claimed is:

1. A method of quantitatively or qualitatively examining and judging chronic fatigue syndrome comprising:
   irradiating a sample derived from an animal with light comprising a continuous wavelength spectrum from 600 nm to 1100 nm,
   measuring an absorption spectrum of a light selected from the group consisting of reflected light, transmitted light, and transmitted and reflected light,
   generating absorption spectral data from the absorption spectrum,
   analyzing the absorption spectral data with multivariate analysis, and
   comparing the multivariate analysis with an analytical model to determine chronic fatigue syndrome in the animal;
   wherein the analytical model comprises data correlating differences in multivariate analysis of absorption spectral data between a normal animal and an animal with chronic fatigue syndrome, and detecting if the absorption spectral data from the sample correlates with the absorption spectral data for the animal with chronic fatigue syndrome.

2. The method of claim 1, wherein the analytical model is a quantitative model prepared by a regression analysis.

3. The method of claim 2, wherein the regression analysis is a partial least squares method.

4. The method of claim 1, wherein the analytical model is a qualitative model prepared by a class discriminant analysis.

5. The method of claim 4, wherein the class discriminant analysis is a soft independent modeling of class analogy method.

6. The method of claim 1, wherein the sample is selected from the group consisting blood, blood plasma, serum, urine, a biological fluid, a tissue, a tissue extract, a part of a living body, an ear, a fingertip, a hand and a foot.

7. The method of claim 1, wherein the continuous wavelength spectrum is decomposed at a predetermined wavelength resolution and the sample is irradiated with light of continuously changing wavelength in increments of predetermined wavelength.

8. The method of claim 1, wherein the absorption spectrum is decomposed at a predetermined wavelength resolution to generate absorption spectral data comprising light of continuously changing wavelength in increments of predetermined wavelength.

9. A test and diagnostic device, comprising:
   a means for irradiating a sample derived from an animal with a light comprising a continuous wavelength spectrum from 400 nm to 2500 nm,
   a means for carrying out spectroscopy, wherein the spectroscopy is selected from the group consisting of prespectroscopy and postspectroscopy,
   a means for measuring an absorption spectrum from light selected from the group consisting of reflected light, transmitted light, and transmitted and reflected light with respect to the light comprising a continuous wavelength spectrum from 400 nm to 2500 nm with which the sample was irradiated,
   a means for generating absorption spectral data from the absorption spectrum, and
   a means for analyzing the absorption spectral data of the sample with multivariate analysis and comparing the multivariate analysis with an analytical model to determine chronic fatigue syndrome in the animal;
   wherein the analytical model comprises data correlating differences in multivariate analysis of absorption spectral data between a normal animal and an animal with chronic fatigue syndrome, and detecting if the absorption spectral data from the sample correlates with the absorption spectral data for the animal with chronic fatigue syndrome patients.

10. The device of claim 9, wherein the analytical model is a quantitative model prepared by a regression analysis.

11. The device of claim 10, wherein the regression analysis is a partial least squares method.

12. The device of claim 9, wherein the analytical model is a qualitative model prepared by a class discriminant analysis.

13. The device of claim 12, wherein the class discriminant analysis is a soft independent modeling of class analogy method.

14. The device of claim 9, wherein the sample is selected from the group consisting blood, blood plasma, serum, urine, a biological fluid, a tissue, a tissue extract, a part of a living body, an ear, a fingertip, a hand and a foot.

15. A non-transitory memory storage medium containing machine readable program code, which, when executed by a processor, causes said processor to perform the process of:
   generating an analytical model to analyze absorption spectral data from an absorption spectrum of a light of a sample irradiated with light comprising a continuous wavelength spectrum from 600 nm to 1100 nm with a multivariate analysis to determine chronic fatigue syndrome in an animal; wherein the analytical model comprises data correlating differences in multivariate analysis of absorption spectral data between a normal animal and an animal with chronic fatigue syndrome,
   determining if absorption spectral data from a sample correlates with absorption spectral data from an animal with chronic fatigue syndrome, and
   analyzing absorption spectral data of a sample with multivariate analysis and comparing the multivariate analysis with an analytical model to determine chronic fatigue syndrome in an animal.

* * * * *